Dec. 2, 1941. LE ROY J. LEISHMAN Re. 21,964

X-RAY STEREOSCOPIC MEANS AND METHOD

Original Filed Oct. 5, 1935 4 Sheets-Sheet 1

INVENTOR:

Le Roy J. Leishman

X-RAY STEREOSCOPIC MEANS AND METHOD

Original Filed Oct. 5, 1935 4 Sheets-Sheet 2

INVENTOR:
Le Roy J. Leishman

X-RAY STEREOSCOPIC MEANS AND METHOD

Original Filed Oct. 5, 1935 4 Sheets-Sheet 3

INVENTOR:
Le Roy J. Leishman

X-RAY STEREOSCOPIC MEANS AND METHOD

Original Filed Oct. 5, 1935 4 Sheets-Sheet 4

INVENTOR:
Le Roy J. Leishman

Reissued Dec. 2, 1941 Re. 21,964

UNITED STATES PATENT OFFICE 21,964

X-RAY STEREOSCOPIC MEANS AND METHOD

Le Roy J. Leishman, Los Angeles, Calif.

Original No. 2,214,621, dated September 10, 1940, Serial No. 43,688, October 5, 1935. Renewed February 13, 1940. Application for reissue September 10, 1941, Serial No. 410,320

14 Claims. (Cl. 250—60)

The invention herein described relates to stereoscopic fluoroscopy and radiography. Some of its objects are: first, to provide practical means for varying the distance between the required two sources of X-rays; second, to afford simple means whereby the separate images produced by the X-rays from these two sources may each be made visible to a different eye; third, to make it possible to control the corresponding shutters for both X-ray tubes from a common control; fourth, to provide means for producing a second image in the space occupied by the grid lines that cross an X-ray picture or fluoroscopic shadowgraph; and fifth, to provide a simple stereoscope for viewing such stereoscopic pictures. Other objects will appear as the specification proceeds.

Figure 1:
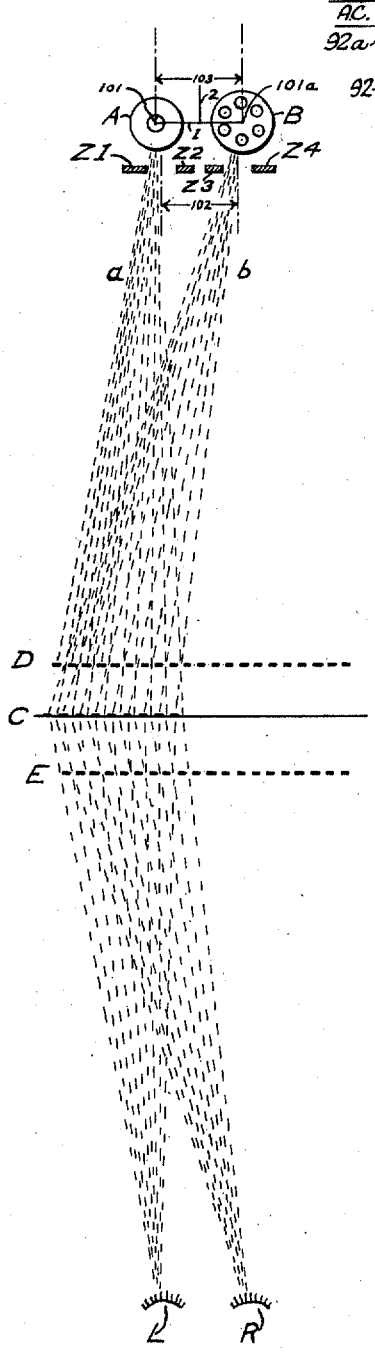
Fig. 1 shows diagrammatically an arrangement whereby two fluoroscopic images are produced in alternate strips by means of a grid opaque to X-rays and obscured each from a different eye by means of a second grid opaque to ordinary light.

In Fig. 1, A and B are X-ray tubes placed side by side with unlike ends together. The anode of one tube is connected to the cathode of the other by wire 1, which is in turn connected to the high potential wire 2. The opposite ends of these tubes, not shown in the figure, are also connected together and to the other side of the high voltage line. X-rays from these tubes fall on the fluorescent screen C through the grating D, the lines of which are so spaced with relation to the screen C and the tubes A and B that the rays *a* from tube A pass between the strips of the grating D and fall on the portions of screen C that are shielded by grid D from the rays *b* from tube B, as shown in the figure. E is a grating consisting of lines or strips alternately opaque and transparent to ordinary light. The spacing of these lines and the distance of grating E from screen C are such that the right eye R sees the portion of the screen C made fluorescent by the rays *a* from tube A, and the left eye L sees the strips of screen C that are made to fluoresce by rays *b* from tube B. Other details of Fig. 1 will be explained further on in this specification.

If a patient to be examined fluoroscopically is placed between the tubes and grid D, the images produced by the X-rays on screen C will be slightly different, due to the distance between the targets where the X-rays originate. This difference is well known in stereoscopic X-ray work. Inasmuch as these images lie in alternate strips, the grating E hides one image from the right eye and the other image from the left eye, thus permitting each eye to see one image only. Due to the difference between these images, the effect is stereoscopic, and the shadows appear to be three-dimensional objects. The observer thus has the sensation of looking right into the body. The grating D may consist of a self-supporting grid of lead or other substance opaque to X-rays, or of a sheet of "Bakelite," aluminum or other material transparent to X-rays having grooves that are etched, engraved or pressed into the surface and then filled in with a material through which X-rays cannot pass, such as powdered lead in a suitable base. A satisfactory grid of this nature may also be made by stringing wire between two parallel notched supports, as is done with the warp in certain kinds of weaving.

Figure 2:
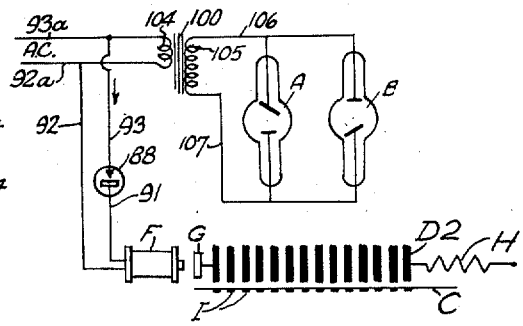
Figs. 2 and 3 illustrate a modification wherein a vibrating Bucky diaphragm or Lysholm grid causes the two X-ray images to fall in alternate strips during alternate halves of the cycle of the alternating current operating the X-ray tubes and the grid vibrating mechanism.
Figure 3:
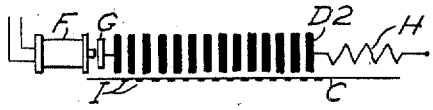

It is well known in radiography and fluoroscopy that the increased sharpness of an image produced with a Bucky diaphragm or Lysholm grid more than compensates for the grid lines on the fluoroscopic screen or X-ray plate. By moving the grid in synchronism with the alternate action of two X-ray tubes connected as in Fig. 1, it is possible to produce two images upon the same surface, each picture occupying the position of the grid lines across the other picture. This is accomplished by the apparatus illustrated in Figs. 2 and 3, in which D2 is a grid composed of lead or similar strips of material with intervening spaces having a greater depth than width. F is one of a series of magnets or solenoids for attracting the iron member G attached to the grid D2. H is one of a plurality of springs for resisting the action of the magnets or other similar electrically operated means. The current that energizes F is a rectified current originating in the same alternating current source as that which operates the X-ray tubes, as indicated in Fig. 2. When alternating current from wire 93a passes through wire 93 in the direction indicated by the arrow, it passes through the half-wave rectifier 88, then through wire 91, magnet F, and wire 92, which connects to 92a, leading to the A. C. source. During the opposite half-cycle of the alternating current, no current will flow through the circuit just described, because it will be in the wrong direction to pass through rectifier 88. Alternating current from wires 92a and 93a is also used to operate the high voltage transformer 100, whose secondary 105 is connected by wires 106 and 107 to the X-ray tubes A and B. Because of the well-known rectifying action of these tubes, they operate on opposite halves of the alternating current cycle. It will thus be evident that during one half of the alternating current cycle, F will be inoperative while the rays from one of the tubes pass between the lead strips of grid D2, leaving dark lines I beneath said strips on screen C as indicated in Fig. 2. During the next half cycle, F will be energized, thus causing grid D2 to move to the position shown in Fig. 3, leaving the previously protected parts of the screen now exposed to the other X-ray tube which is now in operation while the first tube remains inoperative on this half of the cycle.

The tubes A and B are of course at some distance from screen C, as indicated in Fig. 1, but they have been placed much closer in Fig. 2 merely to save space; and it should be understood that the electrical relationship between the tubes and the grid-actuating means, F, is the only feature of the tubes intended to be indicated by Fig. 2.

The necessity for rectifying the current to F can be obviated by polarizing F so that it operates only on alternate halves of the cycles of an alternating current. Many other electrically operated means could be provided to vibrate the grid D2, such as a synchronous motor revolving an eccentric connected to the grid.

If an object to be X-rayed is placed between an assembly like that of Fig. 2 and a pair of X-ray tubes connected and positioned as shown in Fig. 1, and if the current to F is in phase with that which operates the tubes, it is obvious that two different shadows will occupy alternate strips on screen C. By placing a grid like that of E, Fig. 1, in front of screen C, Fig. 2 or 3, these images may be seen each by the proper eye only, and the effect will be sterescopic.

Figure 4:
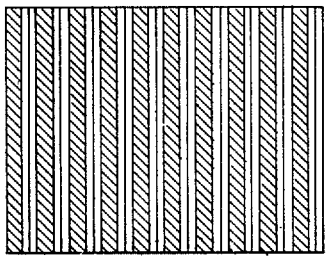
Fig. 4 shows a transparent screen of alternate differently colored strips. In one modification of the invention, this colored screen replaces the grid that is opaque to ordinary light in Fig. 1.

Fig. 4 shows a screen of alternate transparent strips of red and green or other suitable colors. Such a screen may be used as a substitute for screen E in the previous figures. The colored lines are of such width that those of one color will register with the lines of one of the images on screen C, while the lines of the other image will lie behind the strips of the other color. If the strips of this alternately colored screen are red and green and the observer wears spectacles having one red and one green glass, the red strips of the screen will all appear black to the eye wearing the green glass and therefore only the image lying behind the green strips can be seen by this eye. Similarly, the eye wearing the red glass will be able to see the other image only.

It will be obvious that stereoscopic X-ray pictures may be taken in alternate strips on the same plate by means of modifications of the apparatus just described, thus eliminating the necessity of using two plates with usual plate changers. In such stereoscopic radiography, screen C, Fig. 1 or 2, is replaced by the plate to be exposed.

Such pictures may be viewed by providing a view box with a grating like E, Fig. 1, or with a transparent screen having alternate strips of a different color, like that illustrated in Fig. 4. In using this latter arrangement, the two eyes must be provided with the colored spectacles described in a foregoing paragraph.

Figure 5:
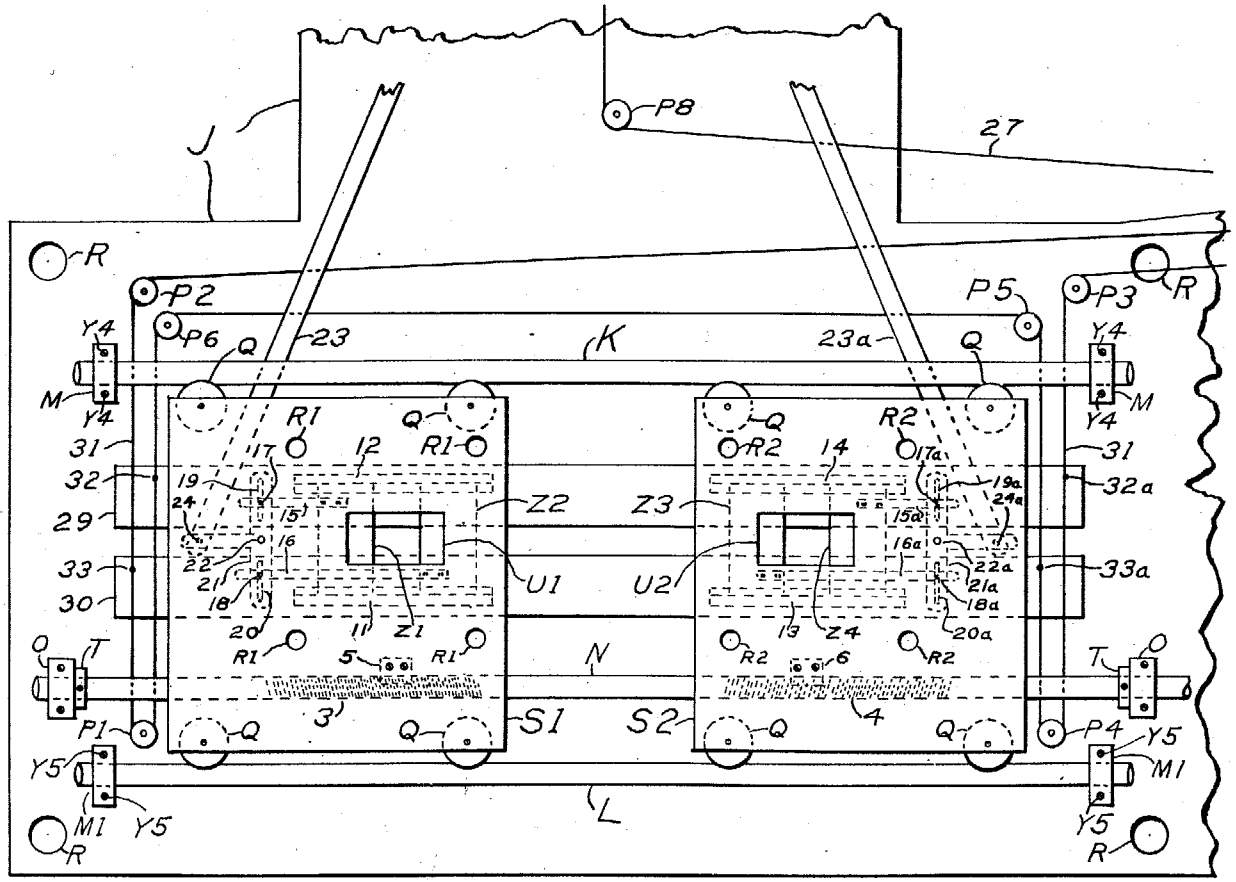
Fig. 5 shows an assembly on which the two X-ray tubes may be mounted, together with the mechanism for operating the shutters and varying the distance between the tubes.
Figure 6:
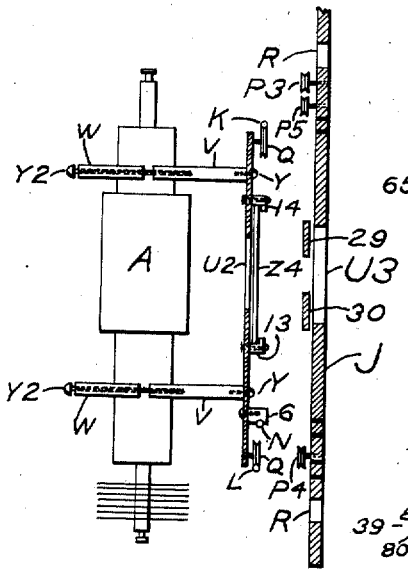
Fig. 6 is a side elevation of Fig. 5, with certain parts omitted for the sake of clearness, and showing an X-ray tube mounted in its supports.

In Fig. 5, J is a supporting plate which may be attached to the tube carriage by means of holes R. Rods K and L are attached to plate J by the supports M and M1 respectively, having connecting screws Y4 and Y5, respectively. Plates S1 and S2 are suspended between rods K and L by means of rollers Q attached to these plates as shown in Figs. 5 and 6. Shaft N, having a right-hand threaded portion 3, Fig. 5, and a left-hand threaded portion 4, is journaled in the supports O and restrained from longitudinal movement by the collars T. Plates S1 and S2 carry half nuts 5 and 6 respectively, which are adapted to engage threaded portions 3 and 4 respectively of the shaft N. The holes R1 and R2, Fig. 5, in plates S1 and S2 respectively are for mounting X-ray tubes. This may be done by means of brackets V, Fig. 6, attached to these plates by means of screws or bolts Y. As shown in this drawing, the tube A is clamped between yoke W and support V by means of screws Y2. Plates S1 and S2 have windows U1 and U2 to permit the passage of X-rays. By turning shaft N, by means to be disclosed later, the threaded portions engage half-nuts 5 and 6, Figs. 5 and 6, causing the plates S1 and S2, with X-ray tubes attached thereto, to move to or from a common center, depending upon whether shaft N is turned to the right or left.

To limit the lateral spread of the X-rays passing through windows U1 and U2, Fig. 5, shutters Z1, Z2, Z3, and Z4 are movably attached to the plates S1 and S2 by means of L-shaped members 11, 12, 13 and 14, attached to the plates, in the manner indicated in Fig. 6. Shutters Z1 and Z2, Fig. 5, are provided with arms 15 and 16, respectively, extending toward the left; and Z4 and Z3 with arms 15a and 16a respectively, extending to the right. Arms 15 and 16 carry pins 17 and 18 respectively, that ride in slots 19 and 20 respectively, in rocker 21 pivoted on pin 22 attached to plate S1. Arms 15a and 16a have pins 17a and 18a respectively, that slide in slots 19a and 20a in rocker 21a having a pivot 22a. The outward projections of rockers 21 and 21a are pivotally attached to levers 23 and 23a respectively by pins 24 and 24a. As will be seen in Fig. 7, levers 23 and 23a are pivotally joined by pin 25, which slides vertically in slot 26 in the upwardly extending part of plate J. A cord 27 attached to pin 25, passes over pulleys P7 and P8 and also around pulley P9, which latter pulley is attached to shaft 28 journaled in the lateral extension of plate J. If shaft 28 is turned to the right, cord 27 will pull up on pin 25, causing levers 23 and 23a to raise the outward arm of rockers 21 and 21a respectively, Fig. 5. This will move the upper arms of these rockers inwardly, along with pins 17 and 17a and the associated shutters Z1 and Z4. This same movement of the rockers will cause the lower pins 18 and 18a to move outward, thus pulling shutters Z2 and Z3 against the respectively associated shutters Z1 and Z4. It will be observed that turning the shaft 28 to the right closes the shutters, and that the shutters are simultaneously opened by turning shaft 28 to the left, and that this is true regardless of how near plates S1 and S2 are to a common center, since the maximum movement of each of these plates is only 2½ inches.

Inasmuch as the rays from the two X-ray tubes must fall on approximately the same area of the fluorescent screen, the windows U1 and U2 must be closer together than the X-ray tubes, as indicated by the relative position of these windows with respect to the holes for mounting the tubes, which holes are assumed to be symmetrically arranged in relation to the tubes. More accurately, the center of the opening between shutters Z1 and Z2 must be slightly to the right of the focal spot on the target in the left tube; and the center of the opening between shutters Z3 and Z4 must be somewhat to the left of the focal spot on the target in the right tube. This difference is indicated in Fig. 1, in which 101 and 101a indicate the positions of the focal spots on the targets of the left and right tubes respectively. The distance 102 from the center of the opening between shutters Z1 and Z2, and the center of the opening between the other pair of shutters Z3 and Z4, is less than the distance 103 between the focal spots 101 and 101a.

Shutters 29 and 30 operate vertically, and are long enough to cross both windows U1 and U2. Shutter 29 is attached to cord 31 at 32 and 32a. Beginning at point 32, cord 31 passes downward and around pulley P1, then up and around pulley P2, thence to the right and around pulley 34, Fig. 7, which turns freely on shaft 28. From pulley 34, cord 31 goes to the left to pulley P3, and then downward, as shown in Fig. 5, around pulley P4, thence up and around P5, and finally around pulley P6, and back to 32. The lower shutter 30 is attached to cord 31 at points 33 and 33a, Fig. 5. If pulley 34 is turned to the right, shutters 29 and 30 will close; and they may be opened by turning 34 to the left.

If the frame J is opaque to X-rays, it is necessary to provide it with a window, U3, Fig. 6, to permit the passage of the rays that emerge between the shutters. This window may be wide enough to accommodate the rays from both tubes, or individual windows may be used. To avoid confusion with other lines, no window of this type is shown in Fig. 5.

Figure 8:
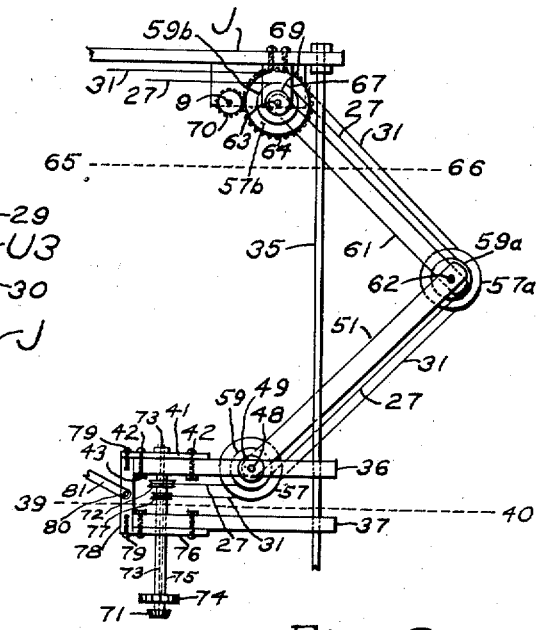
Fig. 8 is a plan view of part of the mechanism whereby the distance between the tubes is automatically varied in accordance with the position of the fluoroscopic screen, and of a remote control for the tube shutters.
Figure 9:
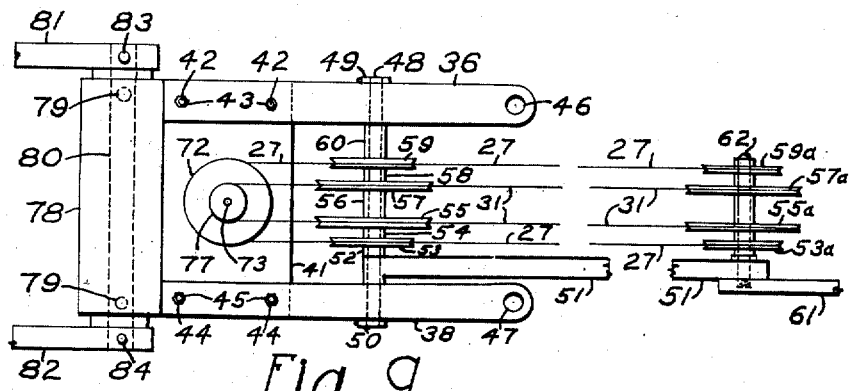
Fig. 9 is a front elevation of the outer end of the control mechanism shown in Fig. 8.
Figure 10:
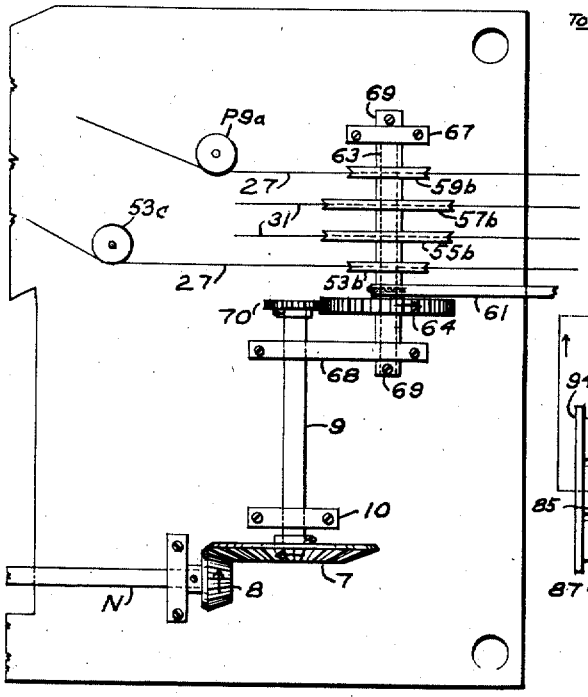
Fig. 10 is a front elevation of the back end of the mechanism shown in Fig. 8, taken along line 65—66, Fig. 8, and shows in addition the various elements whereby motion is transmitted to the movable parts illustrated in Figs. 5 and 7.

Figures 8, 9, and 10 illustrate, among other things, an automatic mechanism for increasing the distance between the two X-ray tubes as the fluoroscopic screen is moved away. To plate J is attached two supporting rods, the uppermost of which, 35, is shown in the plan view, Fig. 8. Rod 35 passes through holes in arms 36 and 37, which are adapted to move along 35. Beneath arm 36, there is another arm 38, shown in Fig. 9, which is a front elevation of the parts that lie behind line 39—40, Fig. 8. To these arms is attached a plate 41, which is fastened to arm 36 by means of bolts 42, passing through 36 and tightened in place by nuts 43, Figs. 8 and 9. Plate 41 is fastened to lower arm 38 by bolts 44 and nuts 45, Fig. 9. 46 is the hole in arm 36 which slides along rod 35, Fig. 8, and 47, Fig. 9, is the corresponding hole in arm 38 which slides along a rod like 35, not shown in Fig. 8 because it lies directly beneath 35.

A shaft 48 passes through arms 36 and 38, Fig. 9, and is held in place by collars 49 and 50. Beginning at the lower end, this shaft 48 supports, in the order named, one end of lever 51, spacer 52, pulley 53, spacer 54, pulley 55, spacer 56, pulley 57, spacer 58, pulley 59 and spacer 60. These pulleys and lever 51 are all free to turn on shaft 48. Lever 51 is attached to lever 61, Fig. 8, by pin 62. The other end of lever 61 is attached to shaft 63, Fig. 10, to which shaft is also attached gear 64. Referring to Fig. 10, which is a front elevation of the parts lying behind line 65—66, Fig. 8, together with additional parts not practical to include in the plan view, it will be seen that shaft 63 is journaled in supports 67 and 68 and held in place by collars 69, 69. As the outer end of lever 61 approaches plate J, shaft 63 and gear 64 turn in the direction indicated by the arrow on gear 64, causing gear 70, shaft 9 and gear 7 to turn in the direction indicated by the arrow on gear 7, which in turn rotates gear 8 in the direction of the arrow shown thereon, thus turning shaft N and bringing the X-ray tubes closer together in the manner previously explained. As the assembly attached to arm 36, Fig. 8, moves away from plate J, the outward end of lever 61 is pulled away from plate J by means of lever 51, thus causing the X-ray tubes to move further apart by means of the mechanism illustrated in Figs. 5 and 10.

Although I prefer the above-described automatic means for varying the distance between the X-ray tubes, it is possible by a modification to attach a flexible shaft directly to shaft N so that the distance between the X-ray tubes may be controlled at the will of the operator from any remote point by means of a knob on the opposite end of the flexible shaft.

Figure 7:
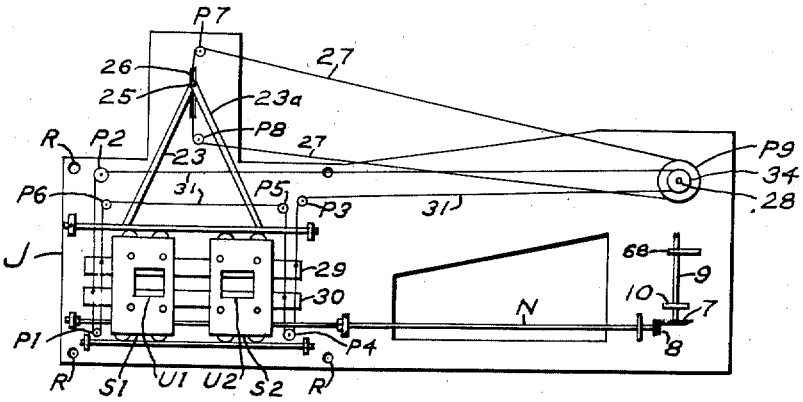
Fig. 7 shows part of the control mechanism for the moving parts illustrated in Fig. 5.

The shutters for the tubes may be controlled from the assembly attached to arm 36, Figs. 8 and 9. Knob 71, Fig. 8, and pulley 72 are both attached to shaft 73, journaled in plate 41. Shaft 73 passes through knob 74 and tube 75, which is attached to knob 74. Tube 75 passes through plate 76 and is attached to pulley 77. Plate 76 is attached to arm 37 and to another arm directly below 37 which therefore does not show in the drawing. Knobs 71 and 74 control the shutters by means of the cords 27 and 31, which in this case are long enough to extend over a system of pulleys, (similar to those used on dental drills) to pulleys 72 and 77 respectively, which are shown in Figs. 8 and 9. In this modification, pulleys P9 and 34, Fig. 7, are omitted, and the following system is substituted: Cord 27, where it would otherwise pass over pulley P9, now passes beneath the substitute pulley P9a, Fig. 10, then around pulley 59b and thence around pulley 59a, Figs. 8 and 9, which latter pulley is free to turn on pin 62. From pulley 59a, Figs. 8 and 9, cord 27 passes around pulleys 59, and then around pulley 72, pulleys 53 and 53a, Fig. 9, 53b and 53c, Fig. 10, from whence it passes to pulley P8, Fig. 7. From here back to pulley P9*a*, cord 27 follows the course originally described. It will thus be evident that shutters Z1, Z2, Z3, and Z4, Fig. 5, can be controlled by knob 71, Fig. 8, which is attached to pulley 72 by shaft 73. When pulley 34, Fig. 7, is eliminated to permit the remote operation of shutters 29 and 30, cord 31, after leaving pulley P2, passes over pulley 34*a*, Fig. 10, around pulley 57*b*, Fig. 10, then around 57*a*, Figs. 8 and 9, pulleys 57, 77, 55, and 55*a*, Fig. 9, and 55*b*, Fig. 10, from whence it follows the course originally described. Inasmuch as pulley 77, is connected to knob 74, by tube 75, as shown in Fig. 8, it follows that shutters 29 and 30 may be controlled by knob 74.

If it is not desired to control the vertical and lateral shutters from a remote point, pulley 34, Fig. 7, may instead be connected to a tube and knob like 75 and 74 respectively, Fig. 8, and pulley P9, Fig. 7, may be connected to shaft 28, which may be extended through the tube and connected to a knob like 71, Fig. 8, in a manner well known in the art.

Member 78, Figs. 8 and 9, is fastened between plates 41 and 76 by screws 79. Shaft 80 passes through member 78, and to this shaft are attached arms 81 and 82, by means of screws 83 and 84, respectively. To the other end of arms 81 and 82, the holder for the fluoroscopic screen is attached in any of the ways well known in the art and therefore neither illustrated nor described here.

Figure 11:
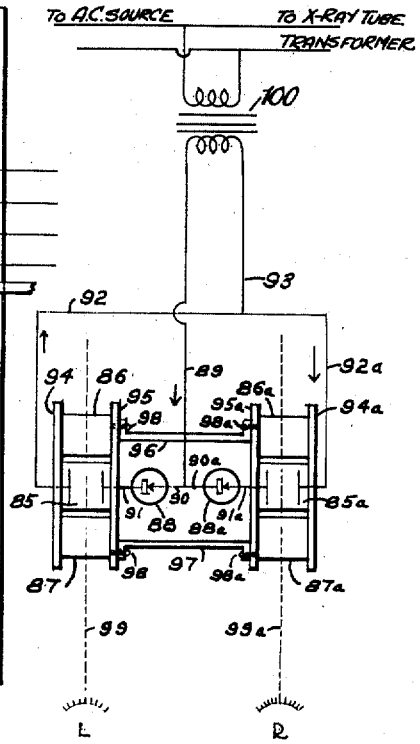
Fig. 11 shows diagrammatically a double Kerr cell assembly with additional parts whereby the right and left eyes may see through their associated optical systems during alternate halves of the cycle of the actuating current.

Inasmuch as X-ray tubes A and B, Fig. 1, emit X-rays on alternate halves of the cycle of the A. C. current, the images that should be independently viewed by the right and left eyes are not simultaneously present on the screen C, but alternate with the operation of the tubes. This has made it possible, in the past, to use synchronous shutters to block the vision of the right and left eyes alternately to prevent them from seeing the images intended for the opposite eyes. In addition to new means already described for attaining this same end without the use of moving parts, another novel method is to provide each eye with a Kerr cell and associated members and energize the Kerr cells alternately by an A. C. current in phase with that which operates the X-ray tubes. Such an arrangement is illustrated in Fig. 11, in which 85 and 85*a* are Kerr cells, 86 and 86*a* are polarizers for polarizing the incident light rays, and 87 and 87*a* are analyzers each capable of adjustment with respect to its cooperating polarizer either to transmit or reject the light polarized by the associated polarizer. These cooperative functions of polarizers and analyzers are well-known in the construction of polariscopes, which are widely used, and in the Kerr cell units as employed in television and telephotography. 88 and 88*a* are rectifying means whereby cells 85 and 85*a* are operated on alternate halves of the cycle of the same A. C. current. Current from transformer 100, passing through wire 89, in the direction of the arrow, will pass through wire 90 and rectifier 88, but will be in the wrong direction to pass through 88*a*. After leaving rectifier 88, said current passes through wire 91, cell 85, wire 92 and wire 93 back to the transformer. During the other half of the cycle, the current from wire 93 will pass through wire 92*a*, (in the direction of the arrow) cell 85*a*, wire 91*a*, rectifier 88*a*, wire 90*a*, and then through wire 89 back to the transformer in an opposite direction to that during the half of the cycle when 85 was energized through the rectifying action of cell 88. Members 94 and 95, and 94*a* and 95*a* support the Kerr cell assemblies, which are paired together by means of brackets 96 and 97, attached to members 95 and 95*a* by screws 98 and 98*a* respectively. L and R are the right and left eyes respectively, looking through the cells along lines 99 and 99*a* respectively.

It is possible, with such Kerr cell assemblies, to arrange the analyzers so that light passes only when the cells are electrically energized, or when they are not energized. In the arrangement shown in Fig. 11, it is immaterial which adjustment of the analyzers is used, providing both analyzers are adjusted the same—that is, so that light passes through whichever cell receives the charge, or fails to pass through whichever one is energized. It will be assumed, however, that the adjustments have been fixed so that light will pass through the charged cell. When current passes through rectifier 88, as is the case during half of the cycle of the A. C. current, the left assembly represented by 87, 85 and 86 becomes transparent, and the left eye L is able to see through the assembly along line 99; and during the opposite half of the cycle the right eye sees through assembly 87*a*, 85*a* and 86*a* along line 99*a*. Inasmuch as these cells are operated by alternating current in phase with that operating the X-ray tubes, the polarity is adjusted so that the right and left eyes see when the left and right tubes, respectively, are operating, thereby carrying out the same objective as that achieved by grating D and E in Fig. 1.

It is obvious that various modifications may be made from the embodiments of the invention herein described without departing from the spirit of the invention.

My claims are:

1. In X-ray apparatus, a combination including a supporting element; two members movably mounted on said element, each member carrying an X-ray tube and a pair of laterally movable shutters; means for moving said members in opposite directions simultaneously; and means for moving the shutters in each pair simultaneously in opposite directions simultaneous with the corresponding movement of the shutters in the other pair.

2. In X-ray apparatus, a combination including two X-ray-tube-carrying members; means for moving said tube-carrying members in opposite directions simultaneously; a pair of shutters movably mounted on each tube-carrying member; means for moving the shutters in each pair simultaneously in opposite directions simultaneous with the corresponding movement of the shutters in the other pair; the distance from the adjoining edges of one pair of shutters when closed to the adjoining edges of the other pair of shutters when closed being less than the distance from the focal spot on the target of one tube to the focal spot on the target of the other tube.

3. In X-ray apparatus, a combination including a supporting member; two supported members each carrying an X-ray tube and a pair of laterally movable shutters; manually controllable means for moving said supported members in opposite directions simultaneously; means for moving the shutters in each pair simultaneously in opposite directions simultaneous with the corresponding movement of the shutters in the other pair; the distance from the adjoining edges of one pair of shutters when closed to the adjoining edges of the other pair of shutters when closed being less than the distance from the focal spot on the target of one tube to the focal spot on the target of the other tube.

4. In X-ray apparatus, a combination including: a source of alternating current; two X-ray tubes adapted to operate on opposite halves of the cycle of said alternating current; a surface that fluoresces when exposed to X-rays; a grid of X-ray resistant strips interposed between said surface and said tubes; and electrical means for vibrating said grid in synchronism with the operation of said tubes; said grid consisting of parallel strips opaque to X-rays, said strips having a spacing substantially equal to their width.

5. In X-ray apparatus, a combination including: two alternately operative sources of X-rays; a surface that fluoresces when exposed to X-rays; a grid comprising parallel strips that are opaque to X-rays, said grid interposed between said sources and said surface; electrical means for vibrating said grid; and a grating comprising strips that are transparent to at least part of the rays of the visible spectrum alternating with strips that are substantially opaque to said latter rays; said latter strips adapted to register with said X-ray opaque strips when said grid is at one end of its vibratory swing, and said transparent strips adapted to register with said X-ray opaque strips when said grid is at the other end of its vibratory swing; said surface interposed between said grid and said grating.

6. In X-ray apparatus, a combination including: a source of alternating current; two X-ray tubes adapted to operate on opposite halves of the cycle of said alternating current; a surface that fluoresces when exposed to X-rays, said surface positioned to receive X-rays from said tubes; and two Kerr cell assemblies each comprising a polarizer and an analyzer; said assemblies adapted to pass light on opposite halves of the cycle of said alternating current so that the fluorescence on said surface that is caused by the X-rays from one tube may be seen through one of said assemblies only, and the fluorescence caused by the X-rays from the other of said tubes may be seen through the other assembly only.

7. In X-ray apparatus, a combination including two members, each carrying an X-ray tube and a pair of laterally movable shutters; a fluoroscopic screen; a movably mounted support for said screen adapted to move in a direction perpendicular to said shutters; and means for moving said members in opposite directions simultaneously, said means operated by the movement of said support.

8. In X-ray apparatus, a combination including a supporting element; two members movably supported on said element, each of said members carrying an X-ray tube and a pair of laterally movable shutters; a supporting structure adapted to move toward and from said shutters; a fluoroscopic screen carried by said structure; means for moving said members in opposite directions simultaneously, said means operated by the movement of said structure; means for varying the opening between each of the two pairs of shutters simultaneously, said shutter-controlling means operable from a manual control carried by said structure.

9. In X-ray apparatus, a combination including a supporting element; two members movably supported on said element, each of said members carrying an X-ray tube; a structure adapted to move in a direction at right angles to the direction of movement of said members; a fluorescent screen mounted on said structure; and automatic means for moving said members in opposite directions simultaneously, said automatic means operated by the movement of said structure.

10. In X-ray apparatus, a combination including two X-ray tubes mounted for relative movement therebetween; two sets of shutters, each set individual to one of said tubes, said sets mounted for relative movement therebetween; and means for moving the individual shutters in both sets simultaneously irrespective of the distance between the sets.

11. In X-ray apparatus, a combination including: a source of alternating current; two X-ray tubes adapted to operate on opposite halves of the cycle of said alternating current; a surface that fluoresces when exposed to X-rays, said surface positioned to receive X-rays from said tubes; two devices individual respectively to the right and left eyes and each constructed and arranged to transmit light that has been polarized substantially in a given plane; and means interposed between said screen and said devices for polarizing the light from said screen and transmitting it to said devices on opposite halves of the cycle of said alternating current so that the fluorescence on said surface that is caused by the X-rays from one tube may be seen through one of said devices only, and the fluorescence caused by the X-rays from the other tube may be seen through the other device only.

12. In X-ray apparatus, a combination including two X-ray tubes; a structure movable with respect to said tubes; a fluorescent screen mounted on said structure; and means operable by the movement of said structure for varying the distance between said tubes.

13. In X-ray apparatus, a combination including two X-ray tubes; means individual to each tube for limiting the spread of the X-rays emitted thereby; a structure movable with respect to said tubes; a fluorescent screen mounted on said structure; and means operable by the movement of said structure for varying the distance between said tubes and between said first mentioned means.

14. In X-ray apparatus, a combination including two movably mounted X-ray tubes; two sets of shutters, each set individual to one of said tubes; a structure movable with respect to said tubes and shutters; a fluorescent screen mounted on said structure; and means operable by the movement of said structure for moving said tubes in opposite directions simultaneously and for varying the distance between said sets.

LE ROY J. LEISHMAN.